US012760253B2

(12) United States Patent
Cannell

(10) Patent No.: US 12,760,253 B2
(45) Date of Patent: Oct. 13, 2026

(54) STERILE DISCONNECT FOR BIOPROCESS SYSTEMS AND METHOD FOR USING SAME

(71) Applicant: Lonza Biologics Inc., Portsmouth, NH (US)

(72) Inventor: Julianna Cannell, Rochester, NH (US)

(73) Assignee: Lonza Biologics Inc., Portsmouth, NH (US)

( * ) Notice: Subject to any disclaimer, the term of this patent is extended or adjusted under 35 U.S.C. 154(b) by 610 days.

(21) Appl. No.: 18/257,156

(22) PCT Filed: Dec. 16, 2021

(86) PCT No.: PCT/US2021/063840
§ 371 (c)(1),
(2) Date: Jun. 13, 2023

(87) PCT Pub. No.: WO2022/133105
PCT Pub. Date: Jun. 23, 2022

(65) Prior Publication Data

US 2024/0026264 A1 Jan. 25, 2024

Related U.S. Application Data

(60) Provisional application No. 63/127,337, filed on Dec. 18, 2020.

(51) Int. Cl.

| | |
|---|---|
| ***C12M 1/00*** | (2006.01) |
| ***C12M 1/12*** | (2006.01) |
| ***C12M 3/00*** | (2006.01) |

(52) U.S. Cl.
CPC ............ *C12M 23/06* (2013.01); *C12M 23/14* (2013.01); *C12M 23/44* (2013.01); *C12M 47/12* (2013.01)

(58) Field of Classification Search
CPC ...... C12M 23/06; C12M 23/14; C12M 23/44; C12M 47/12; C12M 23/28; C12M 23/40;
(Continued)

(56) References Cited

U.S. PATENT DOCUMENTS 5,520,218 A * 5/1996 Hlavinka ............ B29C 66/1122 138/104
7,722,733 B2 * 5/2010 Tomasetti .............. B23K 26/18 156/273.7
(Continued)

FOREIGN PATENT DOCUMENTS

JP 2004073084 3/2004
WO WO2014012584 1/2014

OTHER PUBLICATIONS

International Search Report and Written Opinion of PCT/US2021/063840 dated Apr. 20, 2022, 12 pages.

*Primary Examiner* — Liban M Hassan
(74) *Attorney, Agent, or Firm* — MEDLER FERRO WOODHOUSE & MILLS PLLC

(57) ABSTRACT

A bioprocess apparatus is disclosed that is capable of efficiently disconnecting large bioprocess tubes in a bioprocess system. The bioprocess apparatus includes a separating collar made from a malleable and rigid material that can be placed over large bioprocess tubes. In one aspect, the separating collar includes a pair of adjacent separating edges that allow the collar to be slidably mounted onto a bioprocess tube. Once positioned on the bioprocessed tube, a cutting operation takes place that goes through the separating collar and the bioprocess tube resulting in a sterile disconnect.

21 Claims, 7 Drawing Sheets

(58) Field of Classification Search
CPC ...... C12M 23/58; C12M 33/00; C12M 23/26; B26D 3/16
See application file for complete search history.

(56) References Cited

U.S. PATENT DOCUMENTS

| | | | | |
|---|---|---|---|---|
| 8,056,583 | B2 * | 11/2011 | Lofving | B23D 21/10 285/15 |
| 8,505,586 | B2 * | 8/2013 | Zumbrum | A61M 39/08 285/15 |
| 11,559,811 | B2 | 1/2023 | Bishop et al. | |
| 2003/0230521 | A1 | 12/2003 | Schick | |
| 2012/0184033 | A1 | 7/2012 | Crimmins et al. | |
| 2013/0274929 | A1 | 10/2013 | Hodge et al. | |
| 2016/0122798 | A1 | 5/2016 | Zhang et al. | |
| 2019/0292507 | A1 | 9/2019 | Stone et al. | |

* cited by examiner

STERILE DISCONNECT FOR BIOPROCESS SYSTEMS AND METHOD FOR USING SAME

RELATED APPLICATIONS

The present application is the National Stage entry of International Patent Application No. PCT/US2021/063840 filed on Dec. 16, 2021, which is based on and claims priority to U.S. Patent Application No. 63/127,337, filed on Dec. 18, 2020, which are incorporated herein by reference.

BACKGROUND

Bioreactors, which are apparatuses in which biological reactions or processes can be carried out on a laboratory or industrial scale, are used widely within the biopharmaceutical industry. Bioreactors can be used to produce all different types of bioproducts. Bioproducts can include, for instance, cell cultures and materials derived from cell cultures including vaccines, beverages, biofuels, bioenergy, biochemicals, antibiotics, amino acids, enzymes, monoclonal antibodies, monomers, proteins, food cultures, biopolymers, alcohols, flavorings, fragrances, and the like.

Cell cultures are typically grown in batch processes where the biological material remains in the bioreactor until the end of the reaction time. In certain of these processes, fluid medium contained within the bioreactor can be periodically or continuously removed and resupplied in order to replenish nutrients contained within the fluid medium and for possibly removing damaging by-products that are produced during the process.

During the growth and harvesting of cell cultures, various fluids are formulated and fed to different process equipment. Such fluids, for instance, can include nutrient mediums, various different types of reagents, buffer formulations, and the like. In addition, fluids are also conveyed between different process components. For example, cell cultures are typically grown in bioreactors and then fed downstream to different purification processes. The purification processes can include chromatography skids, filtration devices, and the like. Each of these different steps of the process can also produce product and byproduct streams that are removed during the process and stored in different containers, such as bioprocess bags.

As the development of biologics continue, the ability to mass produce cell cultures in large volumes in order to produce bioproducts is imperative. The recent coronavirus pandemic, for instance, has further illustrated the need for robust processes for producing biologic products. For example, vaccines are currently being produced and tested against the coronavirus strain. Many of these vaccines are based upon biological products obtained from microorganisms, such as messenger RNA therapeutic deliveries. Once a vaccine has been tested and approved, it will be necessary to produce conceivably billions of doses of the vaccine. Thus, there is a need to produce large scale cell culture systems that operate reliably and efficiently.

During the transfer of fluids in larger scale biological processes, larger bioprocess tubes are needed in order to accommodate the volumetric flow rates of the fluids. After fluid transfer, many of these bioprocess tubes must then be disconnected from the different process equipment. Currently, the only solution for connecting and disconnecting larger bioprocess tubes is to purchase bioprocess tubes with automatic disconnects or to install disconnects on the tube. These disconnect devices, however, can form weakened areas along the bioprocess tube and are susceptible to leakage during high pressure operations. In addition, not only are the disconnect devices expensive, but they also provide no ability to make adjustments regarding the location on the bioprocess tube where a disconnection may be desired. Consequently, preassembled disconnect devices are not only impractical, but can also reduce the efficiency of the overall process.

In view of the above, a need exists for a system and method for easily disconnecting mid-scale and large scale bioprocess tubes in a biological process.

SUMMARY

The present disclosure is generally directed to a system and method for growing, harvesting and purifying cell cultures and bioproducts produced therefrom. More particularly, the present disclosure is directed to a bioprocess system and method capable of producing relatively large batches of biological materials. The components contained within the system are all sized for high throughputs in order to produce all different types of beneficial bioproducts, including vaccines for different viruses. In accordance with the present disclosure, the bioprocess method and system include relatively large bioprocess tubes that convey fluids and connect the different components. The present disclosure is directed to a method of disconnecting the bioprocess tubes after fluid flow in an efficient and sterile manner.

For example, in one aspect, the present disclosure is directed to a bioprocess system comprising a first bioprocess device and a second bioprocess device. A bioprocess tube is in fluid communication with the first bioprocess device and the second bioprocess device. The bioprocess tube comprises a thermoplastic elastomer. The bioprocess tube defines a hollow passageway having an internal diameter, an external diameter, and an external surface. The internal diameter of the bioprocess tube is greater than about 260 mm, such as greater than about 280 mm, such as greater than about 300 mm, such as greater than about 320 mm, such as greater than about 340 mm, such as greater than about 360 mm, such as greater than about 380 mm, such as greater than about 400 mm. In accordance with the present disclosure, the system further includes a separating collar for facilitating cutting of the bioprocess tube for disconnecting the first bioprocess device from the second bioprocess device. The separating collar is slidably mounted on the exterior surface of the bioprocess tube. The separating collar has a cylindrical shape and has a length that extends from a first end to a second and opposite end. The separating collar is made from a rigid and malleable material. The separating collar defines at least one pair of adjacent separating edges that extend over the length of the collar. The pair of adjacent separating edges allow the separating collar to be installed and removed from a bioprocess tube. For instance, in one aspect, pair of adjacent separating edges form a slit that extends over the length of the collar.

The separating device can be made from various different materials, such as metallic materials, polymer materials, and the like. The separating collar can be made from a single layer of material or can be made from multiple layers of material. In one embodiment, the separating collar can be made from aluminum. During cutting of the bioprocess tube, a cutting device is used to cut the separating collar and the underlying tube. During cutting, the separating collar and bioprocess tube are compressed. The separating collar is made from a material with sufficient rigidity and malleability such that after cutting the bioprocess tube, the separating collar maintains the open ends of the bioprocess tube in a closed configuration. Consequently, the separating collar is made from a material that is able to withstand the natural biasing forces of the bioprocess tube once the clamping action of the cutting tool is released.

As described above, the separating collar can define a slit along the length of the collar. The slit can have a width, in one aspect, of greater than about 0.5 mm, such as greater than about 1 mm, such as greater than about 1.5 mm, such as greater than about 2 mm, and less than about 5 mm, such as less than about 3 mm. In another aspect, the slit can be wider. For instance, the slit can have a width of greater than about 3 mm, such as greater than about 10 mm, such as greater than about 20 mm, such as greater than about 30 mm, and generally less than about 100 mm. In general, the slit should have a width that facilitates opening the collar so as to place the collar around a bioprocess tube. The length of the separating collar can generally be from about 600 mm to about 3000 mm.

In an alternative embodiment, the opposite ends of the separating collar can overlap along the slit. For example, the opposite free ends of the separating collar can overlap by greater than about 1 mm, such as greater than about 5 mm, and generally less than about 300 mm, such as less than about 15 mm.

In still another alternative embodiment, the separating collar comprises a first collar member and a separate second collar member. The first and second collar members cooperate together to form the cylindrical shape. In this embodiment, the separating collar can form two pairs of adjacent separating edges where the first collar member intersects the second collar member.

The present disclosure is also directed to a process for separating a bioprocess tube contained in a bioprocess. The method includes placing a separating collar on an exterior surface of a bioprocess tube. The bioprocess tube is made from a thermoplastic elastomer and has an internal diameter of greater than about 260 mm, such as greater than about 300 mm. The separating collar is slidably mounted on the exterior surface of the bioprocess tube. The separating collar has a cylindrical shape having a length. At least one pair of adjacent separating edges extend over the length of the separating collar. The pair of adjacent separating edges is for allowing the separating collar to be installed and removed from the bioprocess tube. The method further includes the step of cutting through the separating collar and the bioprocess tube to produce a first free end and a second free end. During cutting, the separating collar and underlying bioprocess tube are deformed, compressing the walls of the bioprocess tube together at each free end. The separating collar is made from a material with sufficient rigidity and malleability to maintain the open ends of the bioprocess tube in a closed state or condition.

In one aspect, the method can further include the step of blocking flow of fluid through the bioprocess tube upstream of the separating device using a flow stop device and blocking flow of fluids through the bioprocess tube downstream of the separating device using a second flow stop device. The flow stop devices, for instance, can comprise clamps and can be installed on each side of the separating device prior to cutting the bioprocess tube.

The present disclosure is also directed to a bioprocess apparatus comprising a separating collar as described above removably and slidably mounted on a bioprocess tube having an internal diameter greater than about 260 mm.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which.

Figure 1:
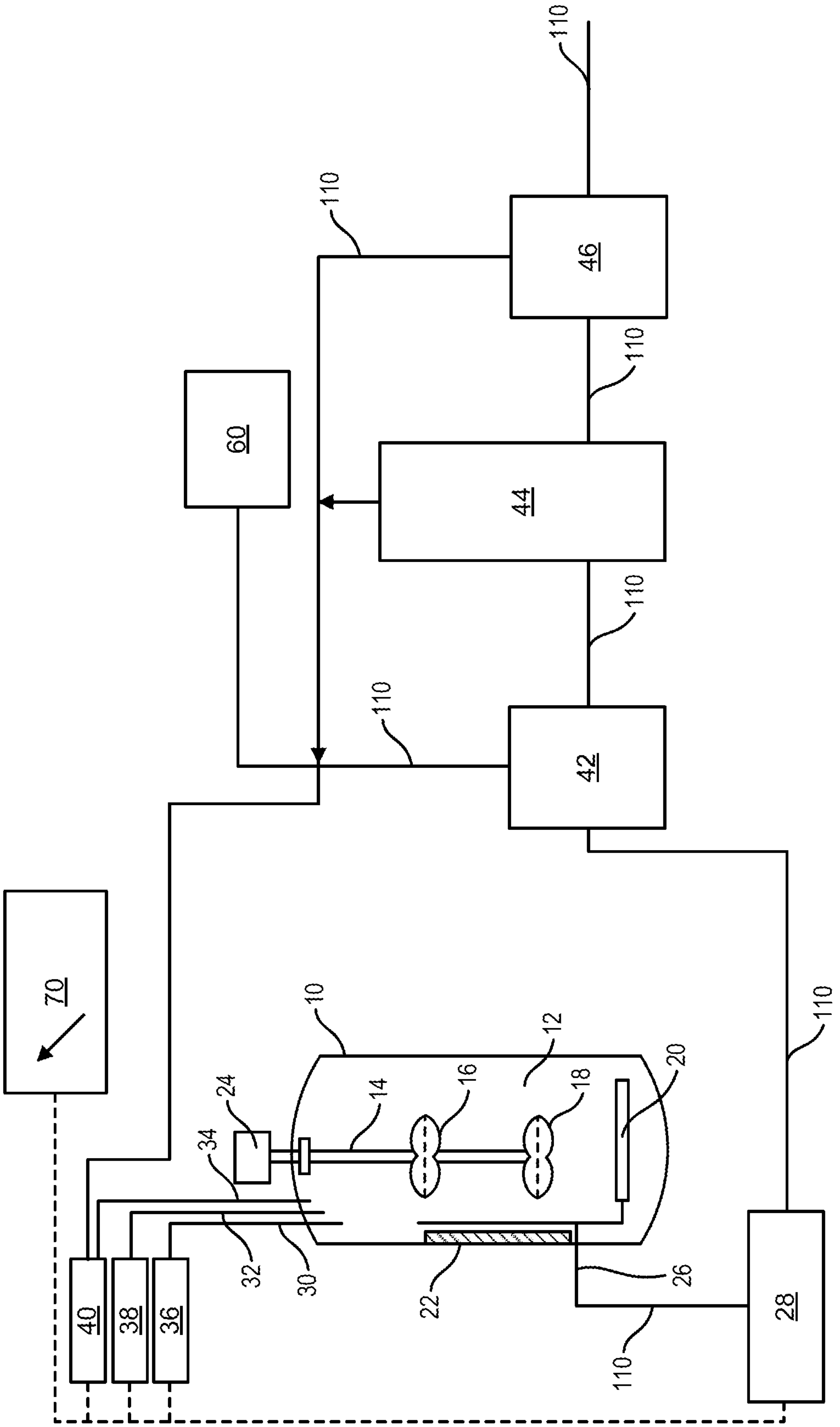
FIG. 1 is a schematic diagram of one embodiment of a bioreactor system that can be used in conjunction with the present disclosure.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only and is not intended as limiting the broader aspects of the present disclosure.

In general, the present disclosure is directed to a system and method for propagating cell cultures, harvesting the cell cultures, purifying the cell cultures and producing a biological product. Many different types of biological products can be produced according to the present disclosure. For instance, the biological product can be a protein or any other metabolite produced by the cell culture. In one embodiment, the cell culture can be used to produce a vaccine for viruses, such as recombinant messenger RNA.

Currently, a major obstacle to the production of biologics, such as vaccines, is the ability to produce the biological products on a larger scale in a reliable manner. In particular, a need exists for bioprocess systems and methods that operate at relatively high throughputs. When over-sizing the equipment and components, various obstacles can exist that may reduce efficiencies. For example, mid-scale and large-scale bioprocess systems need bioprocess tubes that have larger sizes and diameters for connecting the different components together. The present disclosure is directed to an efficient way to disconnect larger bioprocess tubes after fluid flow in order to isolate a component in the system and/or to collect a product or a byproduct in, for instance, a bioprocess bag.

For exemplary purposes only, FIG. 1 illustrates one example of a bioprocess system that may incorporate the elements of the present disclosure for connecting and disconnecting the various different components and bioprocess devices. The bioreactor system includes a bioreactor 10. In general, the system and process of the present disclosure can use any suitable bioreactor. The bioreactor, for instance, may comprise a fermenter, a stirred-tank reactor, an adherent bioreactor, a wave-type bioreactor, a disposable bioreactor, and the like. In the embodiment illustrated in FIG. 1, the bioreactor 10 comprises a hollow vessel or container that includes a bioreactor volume 12 for receiving a cell culture within a fluid growth medium. As shown in FIG. 1, the bioreactor system can further include a rotatable shaft 14 coupled to an agitator such as dual impellers 16 and 18 and to a motor 24.

The bioreactor 10 can be made from various different materials. In one embodiment, for instance, the bioreactor 10 can be made from metal, such as stainless steel. Alternatively, the bioreactor 10 may comprise a single use bioreactor made from a rigid polymer or a flexible polymer film.

The bioreactor 10 can have any suitable volume. In general, however, the bioreactor 10 has a volume of greater than about 5 L, such as greater than about 50 L, such as greater than about 100 L, such as greater than about 500 L, such as greater than about 700 L, such as greater than about 1000 L, such as greater than about 1500 L, such as greater than about 2000 L, such as greater than about 2500 L, such as greater than about 3000 L, such as greater than about 3500 L, such as greater than about 4000 L, such as greater than about 4500 L, such as greater than about 5000 L. The volume of the bioreactor 10 can be even greater than about 7000 L, such as greater than about 10,000 L, such as greater than about 15,000 L, such as greater than about 20,000 L. The volume of the bioreactor 10 is generally less than about 50,000 L, such as less than about L.

In addition to the impellers 16 and 18, the bioreactor 10 can include various additional equipment, such as baffles, spargers, gas supplies, heat exchangers or thermal circulator ports, and the like which allow for the cultivation and propagation of biological cells. For example, in the embodiment illustrated in FIG. 1, the bioreactor 10 includes a sparger 20 and a baffle 22.

As shown in FIG. 1, the bioreactor 10 also includes a plurality of ports. The ports can allow supply lines and feed lines into and out of the bioreactor 10 for adding and removing fluids and other materials. In addition, the one or more ports may be for connecting to one or more probes for monitoring conditions within the bioreactor 10. In addition, the bioreactor 10 and be placed in association with a load cell for measuring the mass of the culture within the bioreactor.

In the embodiment illustrated in FIG. 1, the bioreactor 10 includes a bottom port 26 connected to an effluent 28 for withdrawing materials from the bioreactor continuously or periodically. Materials can be withdrawn from the bioreactor 10 using any suitable method. For instance, in an alternative embodiment, an effluent can be removed from the bioreactor 10 from the top of the bioreactor using a dip tube. In addition, the bioreactor 10 includes a plurality of top ports, such as ports 30, 32, and 34. Port 30 is in fluid communication with a first fluid feed 36, port 32 is in fluid communication with a second feed 38 and port 34 is in fluid communication with a third feed 40. The feeds 36, 38 and 40 are for feeding various different materials to the bioreactor 10, such as a nutrient media.

As shown in FIG. 1, the bioreactor can be in communication with multiple nutrient feeds. In this manner, a nutrient media can be fed to the bioreactor containing only a single nutrient for better controlling the concentration of the nutrient in the bioreactor during the process. In addition or alternatively, the different feed lines can be used to feed gases and liquids separately to the bioreactor.

Once a cell culture has been propagated in the bioreactor 10, in one embodiment, the cell culture is fed to a harvest system for harvesting a bioproduct. Not shown, for instance, the system may include a harvest tank, and a centrifuge. In many systems, the bioproduct being harvested can then be fed to downstream purification processes. For example, in FIG. 1, the bioproduct harvested from the bioreactor 10 can be fed to a first filtration device 42, a chromatography device 44, and a second filtration device 46. It should be understood that the system illustrated in FIG. 1 is merely exemplary and the system can include more than one chromatography device, less than two filtration devices or more than two filtration devices as desired.

The filtration devices 42 and 46 may include a variety of filtration mechanisms. For example, in one embodiment, one of the filtration devices may comprise a tangential flow filtration (TFF) device. A tangential flow filtration device, for instance, may enable the diafiltration of the product stream. A tangential flow filtration device may include two stages; volume reduction and diafiltration. During the volume reduction step, the bulk volume of the cell culture medias is filtered out through the permeate side of the filter until a desired product concentration is reached in the holding tank. In a diafiltration stage following the volume reduction stage, the concentrated product is washed with a fluid, such as a buffer, to remove cell culture or harvest media components that are undesired or are unacceptable. Further volume reduction may also be carried out after diafiltration to reach a desired product density.

In one embodiment, the filtration devices 42 and 46 may use ultrafiltration. During ultrafiltration, the product stream is fed through a semipermeable membrane. Suspended solids and solutes of high molecular weight are retained as a retentate, while water and low molecular weight solutes pass through the membrane as the permeate. Ultrafiltration is particularly well suited to purifying and concentrating protein solutions. In one embodiment, ultrafiltration can be used with diafiltration as described above. The chromatography device 44 as shown in FIG. 1 may use various different chromatography methods such as affinity chromatography, gel filtration chromatography, ion exchange chromatography, reversed phase chromatography, hydrophobic interaction chromatography, and the like.

The process and system of the present disclosure, for instance, can use any suitable chromatography method.

Similar to the filtration devices 42 and 46, the chromatography device 44 may also need a buffer for proper operation of the device.

As shown in FIG. 1, the system can further include a buffer device 60 that stores and/or formulates buffers for feeding to the different components.

As shown in FIG. 1, the system can further include a controller 70. The controller may comprise one or more programmable devices or microprocessors. As shown, the controller 70 can be in communication with the one or more feeds 36, 38 and 40 and with one or more effluents 28.

In addition to the bioprocess devices illustrated in FIG. 1, various other bioprocess devices can be incorporated into the system. For instance, the system can include membrane devices, cation exchange devices, virus reduction filtration devices, and the like.

As shown in FIG. 1, each of the bioprocess devices can be in fluid communication with each other using various different bioprocess tubes 110. In addition, various different bioprocess devices contained within the system can also produce a byproduct stream that can be collected in a bioprocess container or bag. A bioprocess tube can provide fluid commination between the bioprocess container and the other bioprocess device.

The present disclosure is generally directed to a bioprocess apparatus that can efficiently disconnect one bioprocess device from another bioprocess device at any location along a bioprocess tube that was previously used to connect the devices for fluid flow. The bioprocess apparatus of the present disclosure is particularly well suited to forming disconnects on bioprocess tubes that are used in mid-scale and large-scale systems. More particularly, the bioprocess apparatus is designed to form a separation along a bioprocess tube that has a relatively large internal diameter. In one aspect, the bioprocess device can be used to produce a sterile disconnect along the bioprocess tube.

Figure 2:
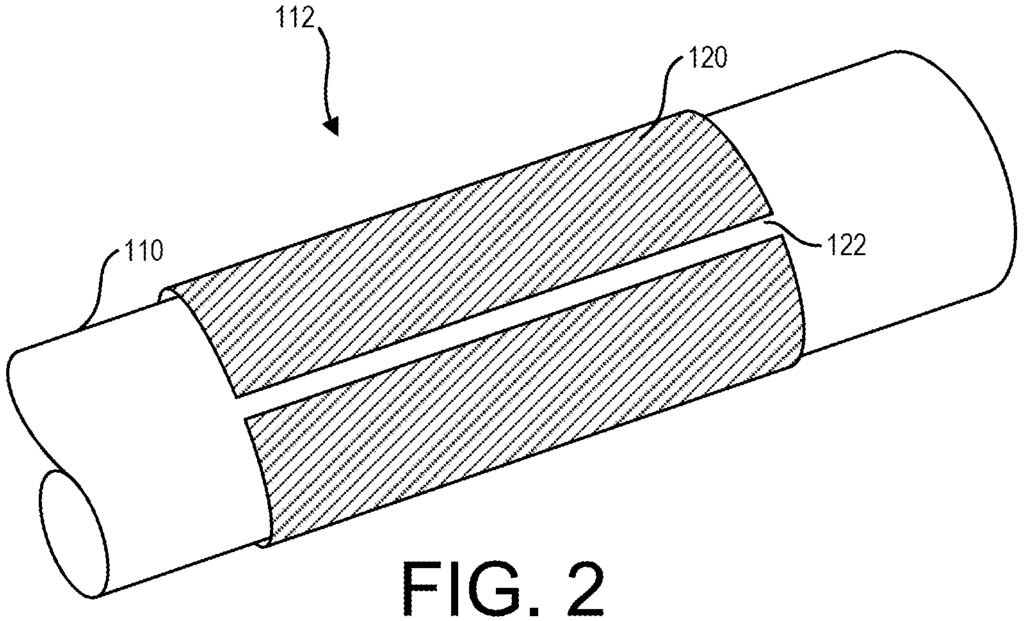
FIG. 2 is a perspective view with cut away portions of one embodiment of a bioreactor apparatus made in accordance with the present disclosure.
Figure 3:
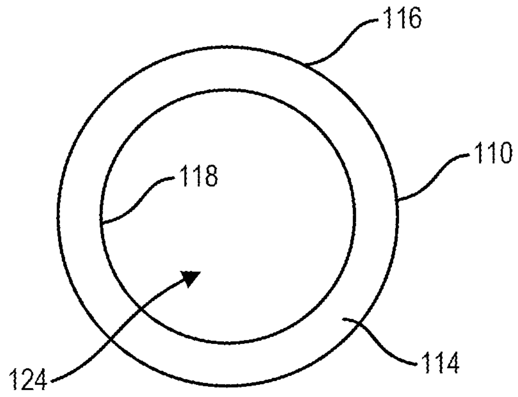
FIG. 3 is a cross-sectional view of a bioprocess tube that may be used in accordance with the present disclosure.

Referring to FIG. 2, one embodiment of a bioprocess apparatus 112 made in accordance with the present disclosure is shown. The bioprocess apparatus 112 includes a bioprocess tube 110 in combination with a separating collar 120. Referring to FIG. 3, a cross-sectional view of the bioprocess tube 110 is illustrated. The bioprocess tube 110 defines an interior passageway 124 that is surrounded by an interior surface 118. The bioprocess tube 110 includes a wall thickness 114 that also defines an exterior surface 116.

The bioprocess tube 110 can be made from a polymer material, particularly a thermoplastic polymer. In one aspect, the bioprocess tube 110 is made from a thermoplastic elastomer. For instance, the bioprocess tube 110 can be made from a silicone polymer. Other elastomers that may be used to produce the bioprocess tube include polyvinyl chloride polymers, polypropylene polymers, polyethylene polymers, or a polyester polymer. As used herein, a polymer can refer to a homopolymer, a copolymer, a block copolymer, a random copolymer, a terpolymer, and the like. For example, polypropylene elastomers can be used that contain a polypropylene homopolymer combined with a polypropylene random copolymer. If desired, the polymer composition used to produce the bioprocess tube 110 can contain a plasticizer.

As described above, the bioprocess tube 110 has a relatively large size capable of conveying significant fluid flow therethrough. The bioprocess tube 110 can have an internal diameter measured from the interior surface 118 and an exterior diameter measured from the exterior surface 116. In general, the internal diameter of the bioprocess tube 110 in accordance with the present disclosure is greater than about 260 mm. For instance, the internal diameter of the bioprocess tube 110 can be greater than about 300 mm, such as greater than about 350 mm, such as greater than about 400 mm, such as greater than about 450 mm, such as greater than about 500 mm, such as greater than about 550 mm, such as greater than about 600 mm, such as greater than about 650, such as greater than about 700 mm, such as greater than about 750 mm, such as greater than about 800 mm, such as greater than about 850 mm, such as greater than about 900 mm, such as greater than about 950 mm, such as greater than about 1000 mm. The internal diameter of the bioprocess tube 110 is generally less than about 2000 mm, such as less than about 1500 mm. In one particular aspect, the internal diameter of the bioprocess tube 110 is from about 260 mm to about 780 mm, including all increments of 5 mm therebetween.

The wall thickness 114 of the bioprocess tube 110 can vary depending upon various factors including the type of thermoplastic polymer used to make the bioprocess tube, and the amount of pressure that may build up within the bioprocess tube 110 during operation. In general, the wall thickness 114 is generally greater than about 5 mm, such as greater than about 6 mm, such as greater than about 7 mm, and generally less than about 12 mm, such as less than about 10 mm, such as less than about 8 mm.

Referring back to FIG. 2, the separating collar 120 of the present disclosure is shown mounted on the exterior surface 116 of the bioprocess tube 110. The separating collar 120 generally has a cylindrical shape that is designed to accommodate the outside diameter of the bioprocess tube 110. The separating collar 120 includes a pair of adjacent separating edges that define a slit 122 that extends along the length of the separating collar 120 from a first end to a second and opposite end.

Figure 6:
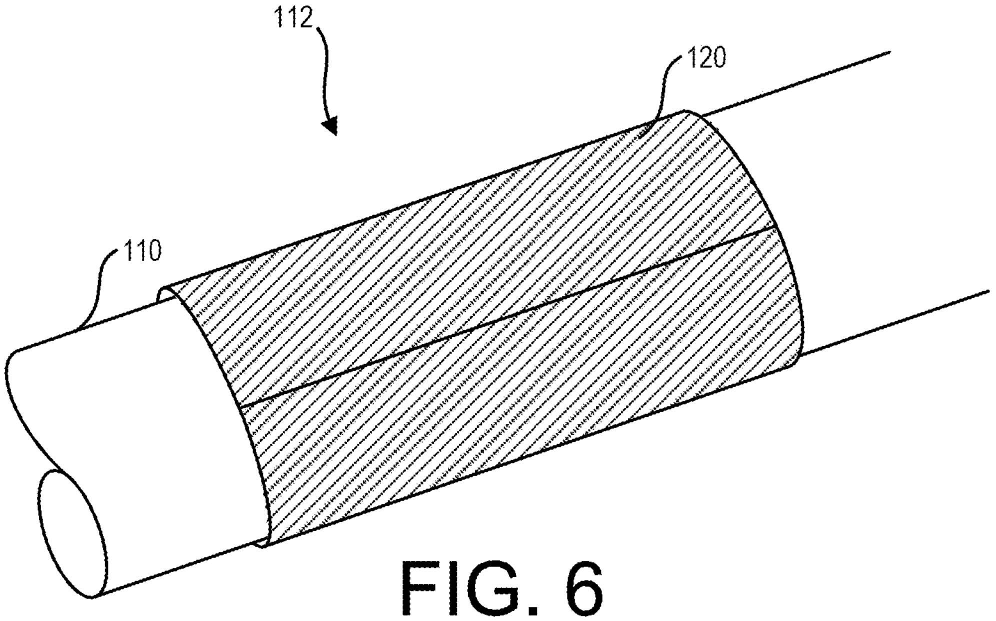
FIG. 6 is a perspective view with cut away portions of another embodiment of a bioreactor apparatus made in accordance with the present disclosure.
Figure 7:
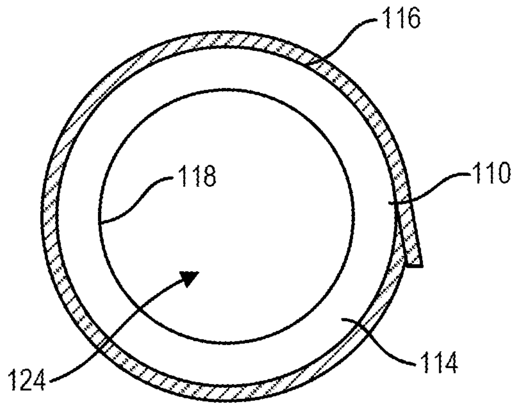
FIG. 7 is a cross-sectional view of the bioprocess apparatus illustrated in FIG. 6.

In an alternative embodiment, the opposing ends of the separating collar 120 along the slit 122 can overlap. For example, as shown in FIG. 6 and FIG. 7, the separating collar 120 defines a slit 122. The opposite ends or edges of the separating collar 120 overlap along the slit 122. The amount of overlap can depend upon various factors. In general, the opposite ends overlap greater than about 1 mm, such as greater than about 5 mm, such as greater than about 8 mm, such as greater than about 10 mm. The amount the opposite ends overlap is generally less than about 300 mm, such as less than about 200 mm, such as less than about 100 mm, such as less than about 50 mm, such as less than about 25 mm, such as less than about 15 mm.

The slit 122 can have various different purposes. In one aspect, for instance, the slit 122 allows the separating collar 120 to be fitted over bioprocess tubes 110 that have different external diameters. In addition, the slit 122 can be used to place the separating collar 120 onto the exterior surface 116 of the bioprocess tube 110. For instance, by grasping opposite ends of the separating collar 120 along the slit 122, one can increase the size of the slit so that the separating collar 120 can be placed over the bioprocess tube 110. In an alternative embodiment, a device or tool made be used that can engage opposite ends of the separating collar along the slit 122 for providing the force necessary for the slit to open up for accommodating a bioprocess tube. In still another embodiment, the separating collar can be manufactured in an open state allowing the collar to be placed over a bioprocess tube. Once placed over the bioprocess tube, the separating collar can then be bended into a desired shape that conforms to the exterior surface of the bioprocess tube.

In addition to the above, the slit 122 also allows the separating device 120 to be slidably mounted onto the bioprocess tube 110. In this manner, the separating collar 120 can be moved to any desired location on the bioprocess tube. The ability to slide the separating collar 120 over the exterior surface 116 of the bioprocess tube 110 provides significant flexibility in determining later the best location to separate the bioprocess tube after fluid flow has stopped.

The width of slit 122 along the length of the separating collar 120 can vary depending upon the type of material used to produce the separating collar 120, the outside diameter of the bioprocess tube 110, and the like. In one aspect, for instance, the slit 122 can be relatively narrow. For instance, the slit can have a width of less than about 3 mm, such as less than about 2 mm, such as less than about 1.5 mm, such as less than about 1 mm, and generally greater than about 0.5 mm, such as greater than about 1 mm. Alternatively, the slit can be wider, especially when the separating collar 120 is to be installed on larger bioprocess tubes. For instance, the width of the slit can be greater than about 3 mm, such as greater than about 10 mm, such as greater than about 20 mm, such as greater than about 30 mm, and generally less than about 100 mm.

The length of the separating collar 120 and therefore the length of the slit can generally be anywhere from about 600 mm to about 10,000 mm and including all increments of 5 mm therebetween. The length of the separating collar 120, for instance, should be sufficient to maintain the bioprocess tube in a closed condition after cutting as will be explained in greater detail below. The upper boundary of the length is not a factor and there may be applications where the length can be greater than about 3000 mm, such as greater than about 5000 mm, such as greater than about 10,000 mm, such as greater than about 15,000 mm.

In FIGS. 2, 6 and 7, the separating collar is made from a single, integral piece of material that includes a single pair of adjacent separating edges that define a slit. In other embodiments, however, the separating collar can be made from multiple pieces of material.

Figure 8:
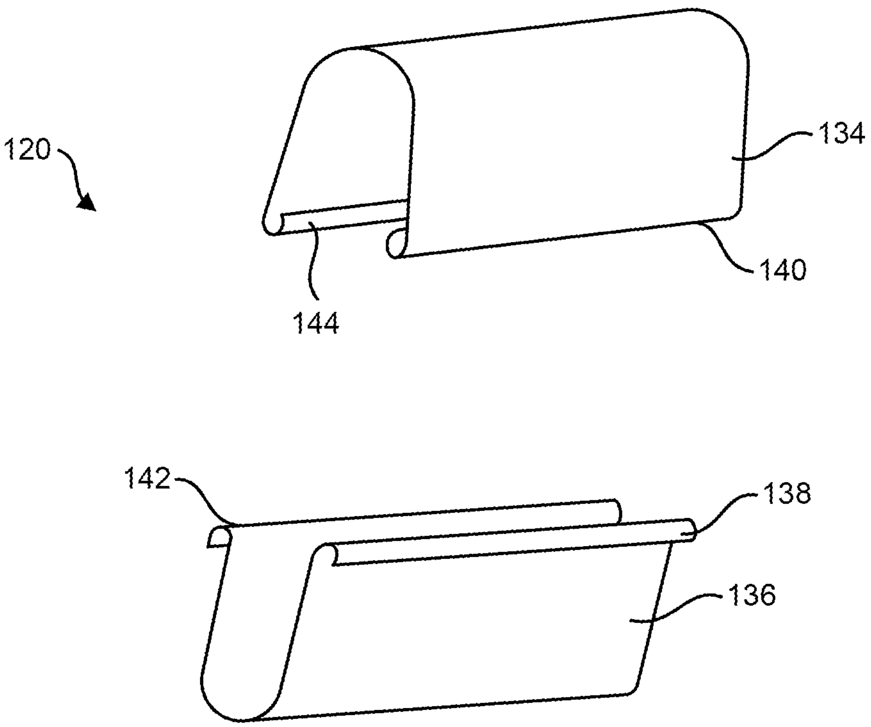
FIG. 8 is a perspective view of an embodiment of a separating collar made in accordance with the present disclosure shown in a disassembled configuration.
Figure 9:
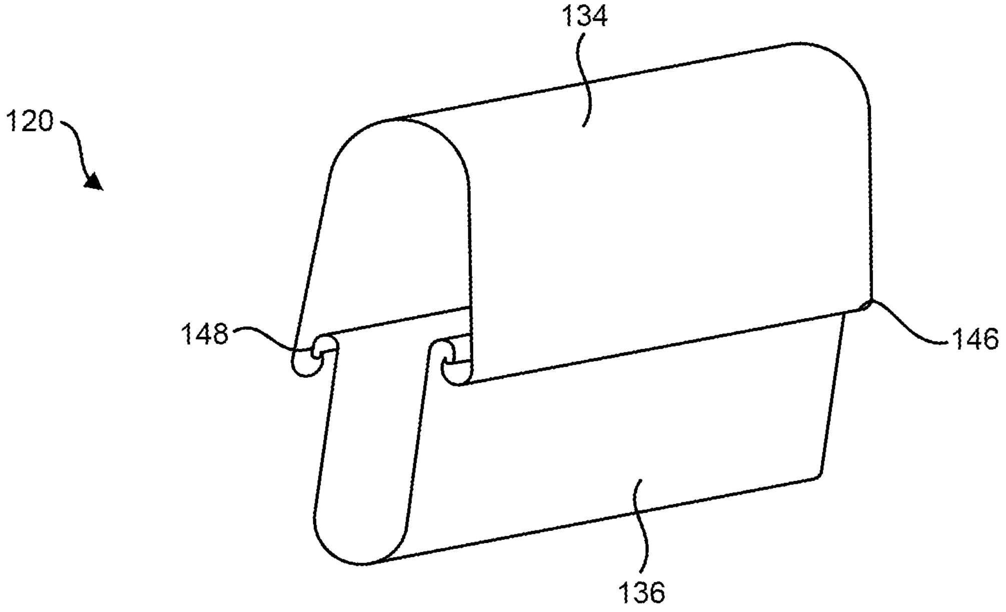
FIG. 9 is a perspective view of the separating collar illustrated in FIG. 8 shown in an assembled configuration.

For example, referring to FIGS. 8 and 9, a separating collar 120 is illustrated that includes a first collar member 134 a second collar member 136. The first collar member 134 and the second collar member 136 are capable of being attached together as shown particularly in FIG. 9. For instance, the separating collar 120 as shown in FIG. 9 defines a first pair of adjacent separating edges 146 and a second pair of adjacent separating edges 148. By being made from two separate pieces of material, the separating collar 120 can easily be placed over a bioprocess tube.

As shown in FIG. 8, the first collar member 134 and the second collar member 136 are capable of being attached together along the separating edges 146 and 148. In general, any suitable attachment device can be used in order to connect the first collar member 134 to the second collar member 136. In the embodiment illustrated in FIG. 8, the first collar member 134 includes curled edges 140 and 144 that are adapted to engage curled edges 138 and 142 on the second collar member 136. It should be understood, however, that any male and female connection can be made between the collar members 134 and 136 along their adjacent edges.

In an alternative embodiment, the first collar member 134 can be connected to the second collar member 136 along a hinge at a first pair of adjacent separating edges. The second pair of adjacent separating edges, on the other hand, can include a connecting device that permits the two edges to connect.

Figure 4:
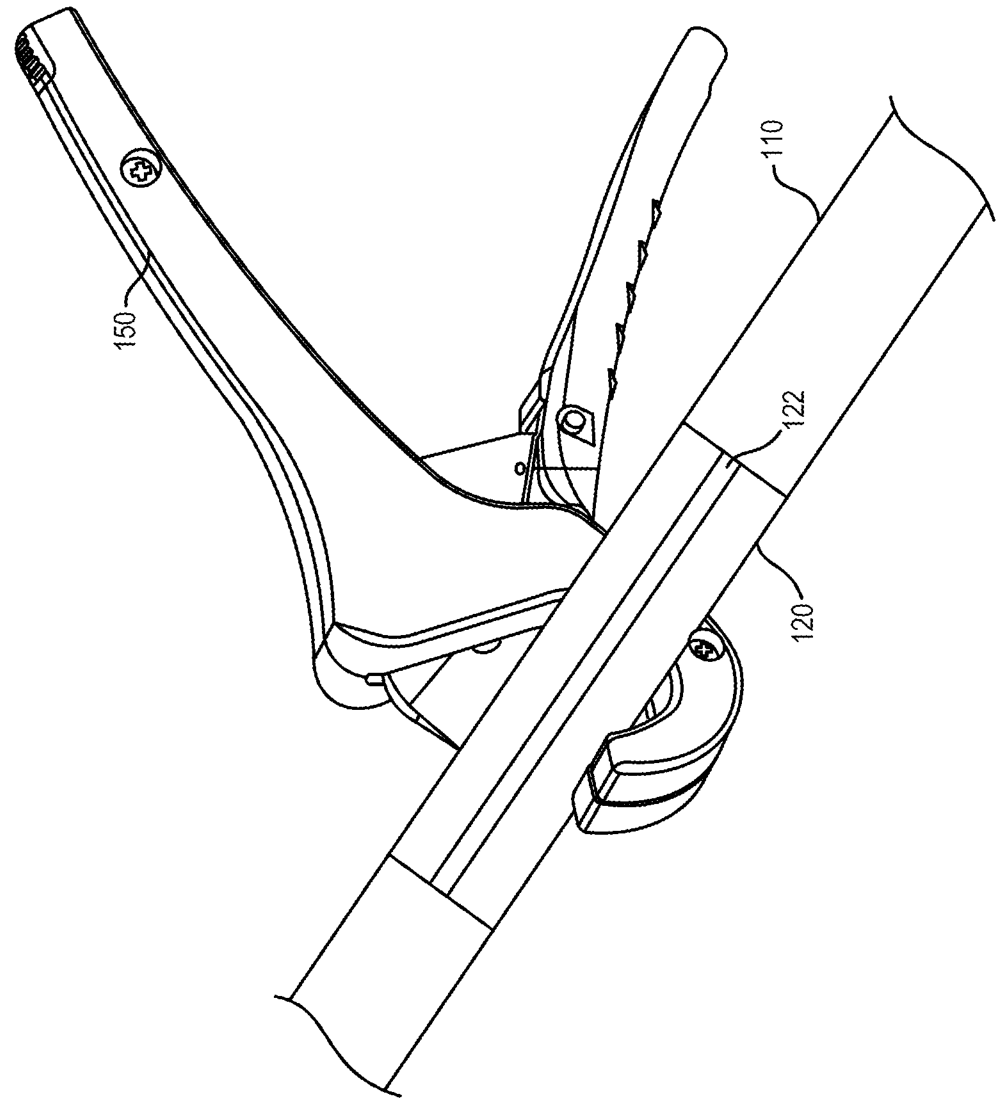
FIG. 4 is a perspective view of one embodiment of a cutting device in conjunction with a bioprocess apparatus of the present disclosure illustrating one manner in which the bioprocess tube may be cut.
Figure 5:
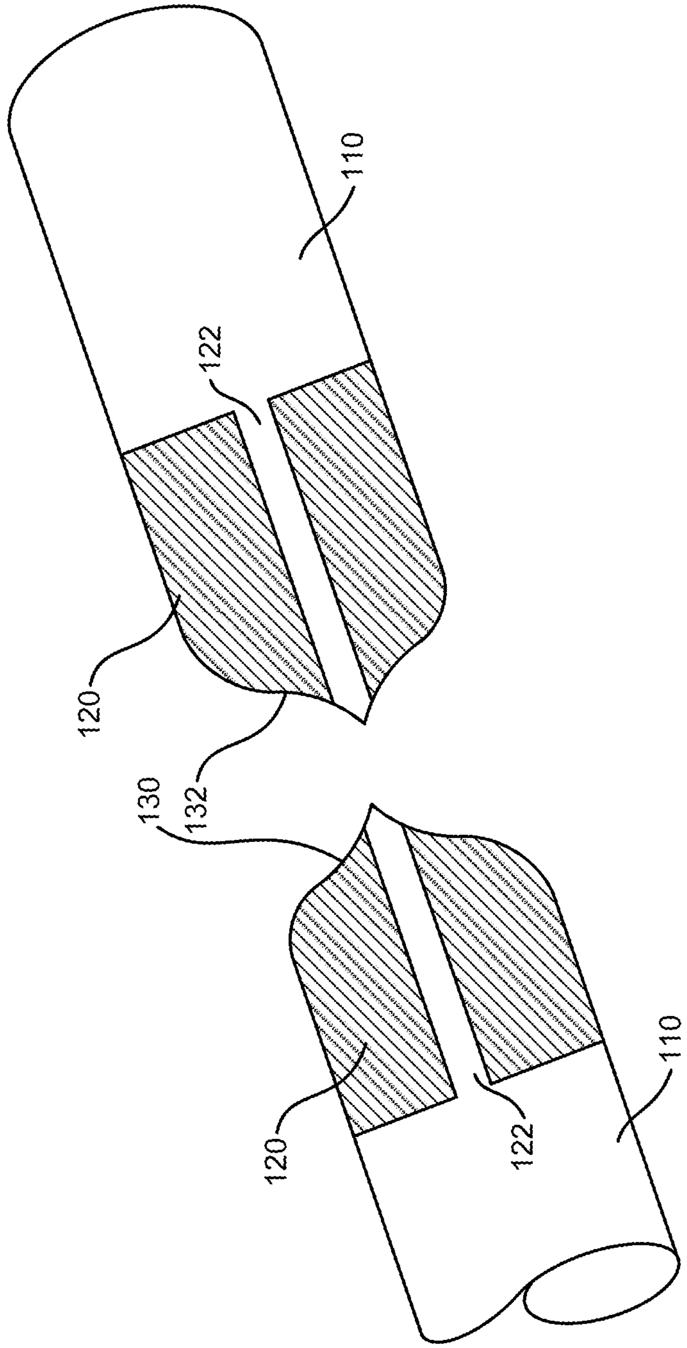
FIG. 5 is a perspective view with cut away portions of the bioprocess apparatus of the present disclosure after a cut has been made.

Referring to FIGS. 4 and 5, one embodiment of a disconnect process in accordance with the present disclosure is illustrated. The bioprocess tube 110 in FIG. 4 can provide fluid communication between two different bioprocess devices. The bioprocess tube 110 can be used for fluid transfer between the two devices. After fluid transfer has terminated, in many operations, it is desirable to disconnect the first bioprocess device from the second bioprocess device. The bioprocess apparatus of the present disclosure provides for an efficient and convenient way to disconnect the two devices from each other.

As explained above, the separating collar 120 is first slidably mounted onto the bioprocess tube 110. The separating collar 120 can then be moved to any desired location where a disconnect operation can take place. Once positioned at the appropriate location, a cutting tool 150 as shown in FIG. 4 can then be used to cut through both the separating device 120 and the underlying bioprocess tube 110. In the embodiment illustrated in FIG. 4, the cutting tool 150 is a handheld device. In other embodiments, however, a motorized device may also be used.

A cutting device 150 is used that compresses the separating collar 120 and bioprocess tube 110 while simultaneously cutting through both materials. For instance, the cutting device 150 can deform the separating device 120 and compress the bioprocess tube squeezing the interior wall of the bioprocess tube together. Once the bioprocess tube 110 and separating collar 120 are compressed together, the cutting device 150 cuts through both materials and forms a first free end 130 and a second free end 132 as shown in FIG. 5. As shown in FIG. 5, the separating collar 120 made in accordance with the present disclosure is made from a material with sufficient malleability and rigidity to deform during cutting and then maintain each free end 130 and 132 in a closed condition. In this manner, the bioprocess apparatus of the present disclosure can produce a sterile disconnect and even an aseptic seal.

In one embodiment, in order to ensure that no fluid drips or spills from the bioprocess tube 110 during the cutting operation, flow stop devices can be installed upstream and downstream from the separating collar 120. The flow stop device can be any suitable clamp capable of cutting off fluid flow through the bioprocess tube 110.

The material used to produce the separating collar 120 should be selected so that the separating collar 120 can be fitted over a bioprocess tube, can be compressed during a cutting process, and can maintain the free ends formed during the cutting process in a closed position. The separating collar 120, for instance, can be made from a polymer material, a reinforced polymer material, a metal, or mixtures thereof. The separating collar 120 can be made from a single layer of material or can have a multilayer design.

In one aspect, the separating collar 120 is made from a metal, such as an aluminum. The thickness of the separating collar 120 can generally be greater than about 0.5 mm, such as greater than about 0.75 mm, such as greater than about 1 mm, such as greater than about 1.1 mm, such as greater than about 1.2 mm, such as greater than about 1.3 mm, such as greater than about 1.4 mm, such as greater than about 1.5 mm. The thickness is generally less than about 4 mm, such as less than about 3 mm, such as less than about 2 mm, such as less than about 1.8 mm.

The separating device 120 can be used at any desired location within a bioprocess system, such as any place shown in the bioprocess system of FIG. 1. In one aspect, the separating collar can be used to disconnect a bioreactor from any upstream or downstream bioprocess device. The separating collar, for instance, can be used to disconnect a bioreactor from a media supply, buffer supply, gas supply, or the like. The separating collar can also be used to disconnect a bioreactor from a downstream device, such as a filtration device.

The separating collar can also be used during harvesting and purification. For instance, the separating device can be used to separate a chromatography device from a filtration device or a filtration device from a process bag.

The devices, facilities and methods described herein are suitable for culturing any desired cell line including prokaryotic and/or eukaryotic cell lines. Further, in embodiments, the devices, facilities and methods are suitable for culturing suspension cells or anchorage-dependent (adherent) cells and are suitable for production operations configured for production of pharmaceutical and biopharmaceutical products—such as polypeptide products, nucleic acid products (for example DNA or RNA), or cells and/or viruses such as those used in cellular and/or viral therapies.

In embodiments, the cells express or produce a product, such as a recombinant therapeutic or diagnostic product. As described in more detail below, examples of products produced by cells include, but are not limited to, antibody molecules (e.g., monoclonal antibodies, bispecific antibodies), antibody mimetics (polypeptide molecules that bind specifically to antigens but that are not structurally related to antibodies such as e.g. DARPins, affibodies, adnectins, or IgNARs), fusion proteins (e.g., Fc fusion proteins, chimeric cytokines), other recombinant proteins (e.g., glycosylated proteins, enzymes, hormones), viral therapeutics (e.g., anti-cancer oncolytic viruses, viral vectors for gene therapy and viral immunotherapy), cell therapeutics (e.g., pluripotent stem cells, mesenchymal stem cells and adult stem cells), vaccines or lipid-encapsulated particles (e.g., exosomes, virus-like particles), RNA (such as e.g. siRNA) or DNA (such as e.g. plasmid DNA), antibiotics or amino acids. In embodiments, the devices, facilities and methods can be used for producing biosimilars.

As mentioned, in embodiments, devices, facilities and methods allow for the production of eukaryotic cells, e.g., mammalian cells or lower eukaryotic cells such as for example yeast cells or filamentous fungi cells, or prokaryotic cells such as Gram-positive or Gram-negative cells and/or products of the eukaryotic or prokaryotic cells, e.g., proteins, peptides, antibiotics, amino acids, nucleic acids (such as DNA or RNA), synthesised by the eukaryotic cells in a large-scale manner. Unless stated otherwise herein, the devices, facilities, and methods can include any desired volume or production capacity including but not limited to bench-scale, pilot-scale, and full production scale capacities.

Moreover and unless stated otherwise herein, the devices, facilities, and methods can include any suitable reactor(s) including but not limited to stirred tank, airlift, fiber, microfiber, hollow fiber, ceramic matrix, fluidized bed, fixed bed, and/or spouted bed bioreactors. As used herein, "reactor" can include a fermentor or fermentation unit, or any other reaction vessel and the term "reactor" is used interchangeably with "fermentor." For example, in some aspects, an example bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and CO2 levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316L or any other suitable stainless steel) and Inconel, plastics, and/or glass.

In embodiments and unless stated otherwise herein, the devices, facilities, and methods described herein can also include any suitable unit operation and/or equipment not otherwise mentioned, such as operations and/or equipment for separation, purification, and isolation of such products. Any suitable facility and environment can be used, such as traditional stick-built facilities, modular, mobile and temporary facilities, or any other suitable construction, facility, and/or layout. For example, in some embodiments modular clean-rooms can be used. Additionally and unless otherwise stated, the devices, systems, and methods described herein can be housed and/or performed in a single location or facility or alternatively be housed and/or performed at separate or multiple locations and/or facilities.

By way of non-limiting examples and without limitation, U.S. Publication Nos. 2013/0280797; 2012/0077429; 2011/0280797; 2009/0305626; and U.S. Pat. Nos. 8,298,054; 7,629,167; and 5,656,491, which are hereby incorporated by reference in their entirety, describe example facilities, equipment, and/or systems that may be suitable.

In embodiments, the cells are eukaryotic cells, e.g., mammalian cells. The mammalian cells can be for example human or rodent or bovine cell lines or cell strains. Examples of such cells, cell lines or cell strains are e.g. mouse myeloma (NSO)-cell lines, Chinese hamster ovary (CHO)-cell lines, HT1080, H9, HepG2, MCF7, MDBK Jurkat, NIH3T3, PC12, BHK (baby hamster kidney cell), VERO, SP2/0, YB2/0, Y0, C127, L cell, COS, e.g., COS1 and COS7, QC1-3, HEK-293, VERO, PER.C6, HeLA, EBI, EB2, EB3, oncolytic or hybridoma-cell lines. Preferably the mammalian cells are CHO-cell lines. In one embodiment, the cell is a CHO cell. In one embodiment, the cell is a CHO-K1 cell, a CHO-K1 SV cell, a DG44 CHO cell, a DUXB11 CHO cell, a CHOS, a CHO GS knock-out cell, a CHO FUT8 GS knock-out cell, a CHOZN, or a CHO-derived cell. The CHO GS knock-out cell (e.g., GSKO cell) is, for example, a CHO-K1 SV GS knockout cell. The CHO FUT8 knockout cell is, for example, the Potelligent® CHOK1 SV (Lonza Biologics, Inc.). Eukaryotic cells can also be avian cells, cell lines or cell strains, such as for example, EBx® cells, EB14, EB24, EB26, EB66, or EBvl3.

In one embodiment, the eukaryotic cells are stem cells. The stem cells can be, for example, pluripotent stem cells, including embryonic stem cells (ESCs), adult stem cells, induced pluripotent stem cells (iPSCs), tissue specific stem cells (e.g., hematopoietic stem cells) and mesenchymal stem cells (MSCs).

In one embodiment, the cells are for cell therapy.

In one embodiment, the cells may include T cells, or immune cells. For instance, the cells can include B cells, natural killer cells, dendritic cells, tumor infiltrating lymphocytes, monocytes, megakaryocytes, or the like.

In one embodiment, the cell is a differentiated form of any of the cells described herein. In one embodiment, the cell is a cell derived from any primary cell in culture.

In embodiments, the cell is a hepatocyte such as a human hepatocyte, animal hepatocyte, or a non-parenchymal cell.

For example, the cell can be a plateable metabolism qualified human hepatocyte, a plateable induction qualified human hepatocyte, plateable Qualyst Transporter Certified™ human hepatocyte, suspension qualified human hepatocyte (including 10-donor and 20-donor pooled hepatocytes), human hepatic kupffer cells, human hepatic stellate cells, dog hepatocytes (including single and pooled Beagle hepatocytes), mouse hepatocytes (including CD-1 and C57BI/6 hepatocytes), rat hepatocytes (including Sprague-Dawley, Wistar Han, and Wistar hepatocytes), monkey hepatocytes (including Cynomolgus or Rhesus monkey hepatocytes), cat hepatocytes (including Domestic Shorthair hepatocytes), and rabbit hepatocytes (including New Zealand White hepatocytes). Example hepatocytes are commercially available from Triangle Research Labs, LLC, 6 Davis Drive Research Triangle Park, North Carolina, USA 27709.

In one embodiment, the eukaryotic cell is a lower eukaryotic cell such as e.g. a yeast cell (e.g., *Pichia* genus (e.g. *Pichia pastoris, Pichia methanolica, Pichia kluyveri*, and *Pichia angusta*), *Komagataella* genus (e.g. *Komagataella pastoris, Komagataella pseudopastoris* or *Komagataella phaffii*), *Saccharomyces* genus (e.g. *Saccharomyces cerevisae, cerevisiae, Saccharomyces kluyveri, Saccharomyces uvarum*), *Kluyveromyces* genus (e.g. *Kluyveromyces lactis, Kluyveromyces marxianus*), the *Candida* genus (e.g. *Candida utilis, Candida cacaoi, Candida boidinii*), the *Geotrichum* genus (e.g. *Geotrichum fermentans*), *Hansenula polymorpha, Yarrowia lipolytica*, or *Schizosaccharomyces pombe*. Preferred is the species *Pichia pastoris*. Examples for *Pichia pastoris* strains are X33, GS115, KM71, KM71H; and CBS7435.

In one embodiment, the eukaryotic cell is a fungal cell (e.g. *Aspergillus* (such as *A. niger, A. fumigatus, A. orzyae, A. nidula*), *Acremonium* (such as *A. thermophilum*), *Chaetomium* (such as *C. thermophilum*), *Chrysosporium* (such as *C. thermophile*), *Cordyceps* (such as *C. militaris*), *Corynascus, Ctenomyces, Fusarium* (such as *F. oxysporum*), *Glomerella* (such as *G. graminicola*), Hypocrea (such as *H. jecorina*), *Magnaporthe* (such as *M. orzyae*), *Myceliophthora* (such as *M. thermophile*), *Nectria* (such as *N. heamatococca*), *Neurospora* (such as *N. crassa*), *Penicillium, Sporotrichum* (such as *S. thermophile*), *Thielavia* (such as *T. terrestris, T. heterothallica*), *Trichoderma* (such as *T. reesei*), or *Verticillium* (such as *V. dahlia*)).

In one embodiment, the eukaryotic cell is an insect cell (e.g., Sf9, Mimic™ Sf9, Sf21, High Five™ (BT1-TN-5B1-4), or BT1-Ea88 cells), an algae cell (e.g., of the genus *Amphora, Bacillariophyceae, Dunaliella, Chlorella, Chlamydomonas, Cyanophyta* (cyanobacteria), *Nannochloropsis, Spirulina*, or Ochromonas), or a plant cell (e.g., cells from monocotyledonous plants (e.g., maize, rice, wheat, or *Setaria*), or from a dicotyledonous plants (e.g., cassava, potato, soybean, tomato, tobacco, alfalfa, *Physcomitrella patens* or *Arabidopsis*).

In one embodiment, the cell is a bacterial or prokaryotic cell.

In embodiments, the prokaryotic cell is a Gram-positive cells such as *Bacillus, Streptomyces Streptococcus, Staphylococcus* or *Lactobacillus*. *Bacillus* that can be used is, e.g. the *B. subtilis, B. amyloliquefaciens, B. licheniformis, B. natto*, or *B. megaterium*. In embodiments, the cell is *B. subtilis*, such as *B. subtilis* 3NA and *B. subtilis* 168. *Bacillus* is obtainable from, e.g., the *Bacillus* Genetic Stock Center, Biological Sciences 556, 484 West 12th Avenue, Columbus OH 43210-1214.

In one embodiment, the prokaryotic cell is a Gram-negative cell, such as *Salmonella* spp. or *Escherichia coli*, such as e.g., TG1, TG2, W3110, DH1, DHB4, DH5a, HMS 174, HMS174 (DE3), NM533, C600, HB101, JM109, MC4100, XL1-Blue and Origami, as well as those derived from *E. coli* B-strains, such as for example BL-21 or BL21 (DE3), all of which are commercially available.

Suitable host cells are commercially available, for example, from culture collections such as the DSMZ (Deutsche Sammlung von Mikroorganismen and Zellkulturen GmbH, Braunschweig, Germany) or the American Type Culture Collection (ATCC).

In embodiments, the cultured cells are used to produce proteins e.g., antibodies, e.g., monoclonal antibodies, and/or recombinant proteins, for therapeutic use. In embodiments, the cultured cells produce peptides, amino acids, fatty acids or other useful biochemical intermediates or metabolites. For example, in embodiments, molecules having a molecular weight of about 4000 daltons to greater than about 140,000 daltons can be produced. In embodiments, these molecules can have a range of complexity and can include posttranslational modifications including glycosylation.

In embodiments, the protein is, e.g., BOTOX, Myobloc, Neurobloc, Dysport (or other serotypes of botulinum neurotoxins), alglucosidase alpha, daptomycin, YH-16, choriogonadotropin alpha, filgrastim, cetrorelix, interleukin-2, aldesleukin, teceleulin, denileukin diftitox, interferon alpha-n3 (injection), interferon alpha-nl, DL-8234, interferon, Suntory (gamma-1a), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alpha, collagenase, carperitide, recombinant human epidermal growth factor (topical gel, wound healing), DWP401, darbepoetin alpha, epoetin omega, epoetin beta, epoetin alpha, desirudin, lepirudin, bivalirudin, nonacog alpha, Mononine, eptacog alpha (activated), recombinant Factor VIII+VWF, Recombinate, recombinant Factor VIII, Factor VIII (recombinant), Alphnmate, octocog alpha, Factor VIII, palifermin, Indikinase, tenecteplase, alteplase, pamiteplase, reteplase, nateplase, monteplase, follitropin alpha, rFSH, hpFSH, micafungin, pegfilgrastim, lenograstim, nartograstim, sermorelin, glucagon, exenatide, pramlintide, iniglucerase, galsulfase, Leucotropin, molgramostirn, triptorelin acetate, histrelin (subcutaneous implant, Hydron), deslorelin, histrelin, nafarelin, leuprolide sustained release depot (ATRIGEL), leuprolide implant (DUROS), goserelin, Eutropin, KP-102 program, somatropin, mecasermin (growth failure), enlfavirtide, Org-33408, insulin glargine, insulin glulisine, insulin (inhaled), insulin lispro, insulin deternir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex' recombinant human luteinizing hormone, dornase alpha, trafermin, ziconotide, taltirelin, diboterminalfa, atosiban, becaplermin, eptifibatide, Zemaira, CTC-111, Shanvac-B, HPV vaccine (quadrivalent), octreotide, lanreotide, ancestirn, agalsidase beta, agalsidase alpha, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-21S, vapreotide, idursulfase, omnapatrilat, recombinant serum albumin, certolizumab pegol, glucarpidase, human recombinant Cl esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexigananacetate, ADI-PEG-20, LDI-200, degarelix, cintredelinbesudotox, Favld, MDX-1379, ISAtx-247, liraglutide, teriparatide (osteoporosis), tifacogin, AA4500, T4N5 liposome lotion, catumaxomab, DWP413, ART-123, Chrysalin, desmoteplase, amediplase, corifollitropinalpha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alpha-n3 (oral), belatacept, transdermal insulin patches, AMG-531, MBP-8298, Xerecept, opebacan, AIDSVAX, GV-1001, LymphoScan, ranpirnase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-I (injectable, vascular disease), BDM-E, rotigaptide, ETC-216, P-113, MBI-594AN, duramycin (inhaled, cystic fibrosis), SCV-07, OPI-45, Endostatin, Angiostatin, ABT- 510, Bowman Birk Inhibitor Concentrate, XMP-629, 99 mTc-Hynic-Annexin V, kahalalide F, CTCE-9908, teverelix (extended release), ozarelix, rornidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, ovarian cancer immunotherapeutic vaccine, SB-249553, Oncovax-CL, OncoVax-P, BLP-25, CerVax-16, multi-epitope peptide melanoma vaccine (MART-1, gp100, tyrosinase), nemifitide, rAAT (inhaled), rAAT (dermatological), CGRP (inhaled, asthma), pegsunercept, thymosinbeta4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 131I-TM-601, KK-220, T-10, ularitide, depelestat, hematide, Chrysalin (topical), rNAPc2, recombinant Factor V111 (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, ACM-9604, linaclotid eacetate, CETi-1, Hemospan, VAL (injectable), fast-acting insulin (injectable, Viadel), intranasal insulin, insulin (inhaled), insulin (oral, eligen), recombinant methionyl human leptin, pitrakinra subcutancous injection, eczema), pitrakinra (inhaled dry powder, asthma), Multikine, RG-1068, MM-093, NBI-6024, AT-001, PI-0824, Org-39141, Cpn10 (autoimmune diseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alpha-n3 (topical), IRX-3, RDP-58, Tauferon, bile salt stimulated lipase, Merispase, alaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, malaria vaccine (virosomes, PeviPRO), ALTU-135, parvovirus B19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBRI-93.02, MTB72F vaccine (tuberculosis), MVA-Ag85A vaccine (tuberculosis), FARA04, BA-210, recombinant plague FIV vaccine, AG-702, OxSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, HA, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3SSIL-3, TST-10088, PRO-1762, Combotox, cholecystokinin-B/gastrin-receptor binding peptides, 111In-hEGF, AE-37, trasnizumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCR1, AT-1100 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV4710, ALG-889, Org-41259, rhCC10, F-991, thymopentin (pulmonary diseases), r(m)CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OSi, AC-162352, PRX-302, LFn-p24 fusion vaccine (Therapore), EP-1043, *S pneumoniae* pediatric vaccine, malaria vaccine, *Neisseria meningitidis* Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH(1-34) (transdermal, ViaDerm), 768974, SYN-101, PGN-0052, aviscumnine, BIM-23190, tuberculosis vaccine, multi-epitope tyrosinase peptide, cancer vaccine, enkastim, APC-8024, GI-5005, ACC-001, TTS-CD3, vascular-targeted TNF (solid tumors), desmopressin (buccal controlled-release), onercept, and TP-9201.

In some embodiments, the polypeptide is adalimumab (HUMIRA), infliximab (REMICADE™), rituximab (RITUXAN™/MAB THERA™) etanercept (ENBREL™), bevacizumab (AVASTIN™), trastuzumab (HERCEPTIN™), pegrilgrastim (NEULASTA™), or any other suitable polypeptide including biosimilars and biobetters.

Other suitable polypeptides are those listed below and in Table 1 of US2016/0097074:

TABLE I

| Protein Product | Reference Listed Drug |
|---|---|
| interferon gamma-1b | Actimmune ® |
| alteplase; tissue plasminogen activator | Activase ®/Cathflo ® |
| Recombinant antihemophilic factor | Advate |
| human albumin | Albutein ® |
| Laronidase | Aldurazyme ® |
| interferon alfa-N3, human leukocyte derived | Alferon N ® |
| human antihemophilic factor | Alphanate ® |
| virus-filtered human coagulation factor IX | AlphaNine ® SD |
| Alefacept; recombinant dimeric fusion protein LFA3-Ig | Amevive ® |
| Bivalirudin | Angiomax ® |
| darbepoetin alfa | Aranesp ™ |
| Bevacizumab | Avastin ™ |
| interferon beta-1a; recombinant | Avonex ® |
| coagulation factor IX | BeneFix ™ |
| Interferon beta-1b | Betaseron ® |
| Tositumomab | BEXXAR ® |
| antihemophilic factor | Bioclate ™ |
| human growth hormone | BioTropin ™ |
| botulinum toxin type A | BOTOX ® |
| Alemtuzumab | Campath ® |
| acritumomab; technetium-99 labeled | CEA-Scan ® |
| alglucerase; modified form of beta-glucocerebrosidase | Ceredase ® |
| imiglucerase; recombinant form of beta-glucocerebrosidase | Cerezyme ® |
| crotalidae polyvalent immune Fab, ovine | CroFab ™ |
| digoxin immune fab [ovine] | DigiFab ™ |
| Rasburicase | Elitek ® |
| Etanercept | ENBREL ® |
| epoietin alfa | Epogen ® |
| Cetuximab | Erbitux ™ |
| algasidase beta | Fabrazyme ® |
| Urofollitropin | Fertinex ™ |
| follitropin beta | Follistim ™ |
| Teriparatide | FORTEO ® |
| human somatropin | GenoTropin ® |
| Glucagon | GlucaGen ® |
| follitropin alfa | Gonal-F ® |
| antihemophilic factor | Helixate ® |
| Antihemophilic Factor; Factor XIII | HEMOFIL |
| adefovir dipivoxil | Hepsera ™ |
| Trastuzumab | Herceptin ® |
| Insulin | Humalog ® |
| antihemophilic factor/von Willebrand factor complex-human | Humate-P ® |
| Somatotropin | Humatrope ® |
| Adalimumab | HUMIRA ™ |
| human insulin | Humulin ® |
| recombinant human hyaluronidase | Hylenex ™ |
| interferon alfacon-1 | Infergen ® |
| eptifibatide | Integrilin ™ |
| alpha-interferon | Intron A ® |
| Palifermin | Kepivance |
| Anakinra | Kineret ™ |
| antihemophilic factor | Kogenate ® FS |
| insulin glargine | Lantus ® |
| granulocyte macrophage colony-stimulating factor | Leukine ®/Leukine ® Liquid |
| lutropin alfa for injection | Luveris |
| OspA lipoprotein | LYMErix ™ |
| Ranibizumab | LUCENTIS ® |
| gemtuzumab ozogamicin | Mylotarg ™ |
| Galsulfase | Naglazyme ™ |
| Nesiritide | Natrecor ® |

TABLE I-continued

| Protein Product | Reference Listed Drug |
|---|---|
| Pegfilgrastim | Neulasta ™ |
| Oprelvekin | Neumega ® |
| Filgrastim | Neupogen ® |
| Fanolesomab | NeutroSpec ™ (formerly LeuTech ®) |
| somatropin [rDNA] | Norditropin ®/Norditropin Nordiflex ® |
| Mitoxantrone | Novantrone ® |
| insulin; zinc suspension; | Novolin L ® |
| insulin; isophane suspension | Novolin N ® |
| insulin, regular; | Novolin R ® |
| Insulin | Novolin ® |
| coagulation factor VIIa | NovoSeven ® |
| Somatropin | Nutropin ® |
| immunoglobulin intravenous | Octagam ® |
| PEG-L-asparaginase | Oncaspar ® |
| abatacept, fully human soluable fusion protein | Orencia ™ |
| muromomab-CD3 | Orthoclone OKT3 ® |
| high-molecular weight hyaluronan | Orthovisc ® |
| human chorionic gonadotropin | Ovidrel ® |
| live attenuated Bacillus Calmette-Guerin | Pacis ® |
| peginterferon alfa-2a | Pegasys ® |
| pegylated version of interferon alfa-2b | PEG-Intron ™ |
| Abarelix (injectable suspension); gonadotropin-releasing hormone antagonist | Plenaxis ™ |
| epoietin alfa | Procrit ® |
| Aldesleukin | Proleukin, IL-2 ® |
| Somatrem | Protropin ® |
| dornase alfa | Pulmozyme ® |
| Efalizumab; selective reversible T-cell blocker | RAPTIVA ™ |
| combination of ribavirin and alpha interferon | Rebetron ™ |
| Interferon beta 1a | Rebif ® |
| antihemophilic factor | Recombinate ® rAHF/ |
| antihemophilic factor | ReFacto ® |
| Lepirudin | Refludan ® |
| Infliximab | REMICADE ® |
| Abciximab | ReoPro ™ |
| Reteplase | Retavase ™ |
| Rituxima | Rituxan ™ |
| interferon alfa-2a | Roferon-A ® |
| Somatropin | Saizen ® |
| synthetic porcine secretin | SecreFlo ™ |
| Basiliximab | Simulect ® |
| Eculizumab | SOLARIS (R) |
| Pegvisomant | SOMAVERT ® |
| Palivizumab; recombinantly produced, humanized mAb | Synagis ™ |
| thyrotropin alfa | Thyrogen ® |
| Tenecteplase | TNKase ™ |
| Natalizumab | TYSABRI ® |
| human immune globulin intravenous 5% and 10% solutions | Venogiobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| Daclizumab | Zenapax ® |
| ibritumomab tiuxetan | Zevalin ™ |
| Somatotropin | Zorbtive ™ (Serostim ®) |

In embodiments, the polypeptide is a hormone, blood clotting/coagulation factor, cytokine/growth factor, antibody molelcule, fusion protein, protein vaccine, or peptide as shown in Table 2.

TABLE 2

| Exemplary Products | | |
|---|---|---|
| Therapeutic Product type | Product | Trade Name |
| Hormone | Erythropoietin, Epoein- | Epogen, Procrit |
| | □ | Aranesp |
| | Darbepoetin□□ | Genotropin, Humatrope, |
| | Growth hormone (GH), | Norditropin, NovIVitropin, |
| | somatotropin | Nutropin, Omnitrope, Protropin, |
| | Human follicle-stimulating | Siazen, Serostim, Valtropin |
| | hormone (FSH) | Gonal-F, Follistim |
| | Human chorionic gonadotropin | Ovidrel |
| | Lutropin-□ | Luveris |
| | Glucagon | GlcaGen |
| | Growth hormone releasing | Geref |
| | hormone (GHRH) | ChiRhoStim (human peptide), SecreFlo |
| | Secretin | (porcine peptide) |
| | Thyroid stimulating hormone | Thyrogen |
| | (TSH), thyrotropin | |
| Blood | Factor VIIa | NovoSeven |
| Clotting/Coagulation | Factor VIII | Bioclate, Helixate, Kogenate, Recombinate, |
| Factors | Factor IX | ReFacto |
| | Antithrombin III (AT-III) | Benefix |
| | Protein C concentrate | Thrombate III |
| | | Ceprotin |
| Cytokine/Growth | Type I alpha-interferon | Infergen |
| factor | Interferon-□n3 (IFN□n3) | Alferon N |
| | Interferon-□1a (rIFN-□□) | Avonex, Rebif |
| | Interferon-□1b (rIFN-□□) | Betaseron |
| | Interferon-□1b (IFN□□) | Actimmune |
| | Aldesleukin (interleukin | Proleukin |
| | 2(IL2), epidermal theymocyte | Kepivance |
| | activating factor; ETAF | Regranex |
| | Palifermin (keratinocyte | Anril, Kineret |
| | growth factor; KGF) | |
| | Becaplemin (platelet-derived | |
| | growth factor; PDGF) | |
| | Anakinra (recombinant IL1 | |
| | antagonist) | |
| Antibody molecules | Bevacizumab (VEGFA mAb) | Avastin |
| | Cetuximab (EGFR mAb) | Erbitux |
| | Panitumumab (EGFR mAb) | Vectibix |
| | Alemtuzumab (CD52 mAb) | Campath |
| | Rituximab (CD20 chimeric | Rituxan |
| | Ab) | Herceptin |
| | Trastuzumab (HER2/Neu | Orencia |
| | mAb) | Humira |
| | Abatacept (CTLA Ab/Fc | Enbrel |
| | fusion) | Remicade |
| | Adalimumab (TNF□□mAb) | Amevive |
| | Etanercept (TNF receptor/Fc | Raptiva |
| | fusion) | Tysabri |
| | Infliximab (TNF□ | Soliris |
| | chimeric mAb) | Orthoclone, OKT3 |
| | Alefacept (CD2 fusion protein) | |
| | Efalizumab (CD11a mAb) | |
| | Natalizumab (integrin | |
| | □4subunit mAb) | |
| | Eculizumab (C5mAb) | |
| | Muromonab-CD3 | |
| Other: | Insulin | Humulin, Novolin |
| Fusion | Hepatitis B surface antigen | Engerix, Recombivax HB |
| proteins/Protein | (HBsAg) | Gardasil |
| vaccines/Peptides | HPV vaccine | LYMErix |
| | OspA | Rhophylac |
| | Anti-Rhesus(Rh) | Fuzeon |
| | immunoglobulin G | QMONOS |
| | Enfuvirtide | |
| | Spider silk, e.g., fibrion | |

In embodiments, the protein is multispecific protein, e.g., a bispecific antibody as shown in Table 3.

TABLE 3

Bispecific Formats

| Name (other names, sponsoring organizations) | BsAb format | Targets | Proposed mechanisms of action | Development stages | Diseases (or healthy volunteers) |
|---|---|---|---|---|---|
| Catumaxomab (Removab ®, Fresenius Biotech, Trion Pharma, Neopharm) | BsIgG: Triomab | CD3, EpCAM | Retargeting of T cells to tumor, Fc mediated effector functions | Approved in EU | Malignant ascites in EpCAM positive tumors |
| Ertumaxomab (Neovii Biotech, Fresenius Biotech) | BsIgG: Triomab | CD3, HER2 | Retargeting of T cells to tumor | Phase I/II | Advanced solid tumors |
| Blinatumomab (Blincyto ®, AMG 103, MT 103, MEDI 538, Amgen) | BiTE | CD3, CD19 | Retargeting of T cells to tumor | Approved in USA<br>Phase II and III<br>Phase II<br>Phase I | Precursor B-cell ALL<br>ALL<br>DLBCL<br>NHL |
| REGN1979 (Regeneron) | BsAb | CD3, CD20 | | | |
| Solitomab (AMG 110, MT110, Amgen) | BiTE | CD3, EpCAM | Retargeting of T cells to tumor | Phase I | Solid tumors |
| MEDI 565 (AMG 211, MedImmune, Amgen) | BiTE | CD3, CEA | Retargeting of T cells to tumor | Phase I | Gastrointestinal adenocancinoma |
| RO6958688 (Roche) | BsAb | CD3, CEA | | | |
| BAY2010112 (AMG 212, Bayer; Amgen) | BiTE | CD3, PSMA | Retargeting of T cells to tumor | Phase I | Prostate cancer |
| MGD006 (Macrogenics) | DART | CD3, CD123 | Retargeting of T cells to tumor | Phase I | AML |
| MGD007 (Macrogenics) | DART | CD3, gpA33 | Retargeting of T cells to tumor | Phase I | Colorectal cancer |
| MGD011 (Macrogenics) | DART | CD19, CD3 | | | |
| SCORPION (Emergent Biosolutions, Trubion) | BsAb | CD3, CD19 | Retargeting of T cells to tumor | | |
| AFM11 (Affimed Therapeutics) | TandAb | CD3, CD19 | Retargeting of T cells to tumor | Phase I | NHL and ALL |
| AFM12 (Affimed Therapeutics) | TandAb | CD19, CD16 | Retargeting of NK cells to tumor cells | | |
| AFM13 (Affimed Therapeutics) | TandAb | CD30, CD16A | Retargeting of NK cells to tumor cells | Phase II | Hodgkin's Lymphoma |
| GD2 (Barbara Ann Karmanos Cancer Institute) | T cells preloaded with BsAb | CD3, GD2 | Retargeting of T cells to tumor | Phase I/II | Neuroblastoma and osteosarcoma |
| pGD2 (Barbara Ann Karmanos Cancer Institute) | T cells preloaded with BsAb | CD3, Her2 | Retargeting of T cells to tumor | Phase II | Metastatic breast cancer |
| EGFRBi-armed autologous activated T cells (Roger Williams Medical Center) | T cells preloaded with BsAb | CD3, EGFR | Autologous activated T cells to EGFR-positive tumor | Phase I | Lung and other solid tumors |
| Anti-EGFR-armed activated T cells (Barbara Ann Karmanos Cancer Institute) | T cells preloaded with BsAb | CD3, EGFR | Autologous activated T-cells to EGFR-positive tumor | Phase I | Colon and pancreatic cancers |
| rM28 (University Hospital Tübingen) | Tandem scFv | CD28, MAPG | Retargeting of T cells to tumor | Phase II | Metastatic melanoma |
| IMCgp100 (Immunocore) | ImmTAC | CD3, peptide MHC | Retargeting of T cells to tumor | Phase I/II | Metastatic melanoma |
| DT2219ARL (NCI, University of Minnesota) | 2 scFv linked to diphtheria toxin | CD19, CD22 | Targeting of protein toxin to tumor | Phase I | B cell leukemia or lymphoma |

TABLE 3-continued

| Bispecific Formats | | | | | |
|---|---|---|---|---|---|
| Name (other names, sponsoring organizations) | BsAb format | Targets | Proposed mechanisms of action | Development stages | Diseases (or healthy volunteers) |
| XmAb5871 (Xencor) | BsAb | CD19, CD32b | | | |
| NI-1701 (NovImmune) | BsAb | CD47, CD19 | | | |
| MM-111 (Merrimack) | BsAb | ErbB2, ErbB3 | | | |
| MM-141 (Merrimack) | BsAb | IGF-1R, ErbB3 | | | |
| NA (Merus) | BsAb | HER2, HER3 | | | |
| NA (Merus) | BsAb | CD3, CLEC12A | | | |
| NA (Merus) | BsAb | EGFR, HER3 | | | |
| NA (Merus) | BsAb | PD1, undisclosed | | | |
| NA (Merus) | BsAb | CD3, undisclosed | | | |
| Duligotuzumab (MEHD7945A, Genentech, Roche) | DAF | EGFR, HER3 | Blockade of 2 receptors, ADCC | Phase I and II<br>Phase II | Head and neck cancer<br>Colorectal cancer |
| LY3164530 (Eli Lily) | Not disclosed | EGFR, MET | Blockade of 2 receptors | Phase I | Advanced or metastatic cancer |
| MM-111 (Merrimack Pharmaceuticals) | HSA body | HER2, HER3 | Blockade of 2 receptors | Phase II<br>Phase I | Gastric and esophageal cancers<br>Breast cancer |
| MM-141, (Merrimack Pharmaceuticals) | IgG-scFv | IGF-1R, HER3 | Blockade of 2 receptors | Phase I | Advanced solid tumors |
| RG7221 (RO5520985, Roche) | CrossMab | Ang2, VEGF A | Blockade of 2 proangiogenics | Phase I | Solid tumors |
| RG7716 (Roche) | CrossMab | Ang2, VEGF A | Blockade of 2 proangiogenics | Phase I | Wet AMD |
| OMP-305B83 (OncoMed) | BsAb | DLL4/VEGF | | | |
| TF2 (Immunomedics) | Dock and lock | CEA, HSG | Pretargeting tumor for PET or radioimaging | Phase II | Colorectal, breast and lung cancers |
| ABT-981 (AbbVie) | DVD-Ig | IL-1α, IL-1β | Blockade of 2 proinflammatory cytokines | Phase II | Osteoarthritis |
| ABT-122 (AbbVie) | DVD-Ig | TNF, IL-17A | Blockade of 2 proinflammatory cytokines | Phase II | Rheumatoid arthritis |
| COVA322 | IgG-fynomer | TNF, IL17A | Blockade of 2 proinflammatory cytokines | Phase I/II | Plaque psoriasis |
| SAR156597 (Sanofi) | Tetravalent bispecific tandem IgG | IL-13, IL-4 | Blockade of 2 proinflammatory cytokines | Phase I | Idiopathic pulmonary fibrosis |
| GSK2434735 (GSK) | Dual-targeting domain | IL-13, IL-4 | Blockade of 2 proinflammatory cytokines | Phase I | (Healthy volunteers) |
| Ozoralizumab (ATN103, Ablynx) | Nanobody | TNF, HSA | Blockade of proinflammatory cytokine, binds to HSA to increase half-life | Phase II | Rheumatoid arthritis |
| ALX-0761 (Merck Serono, Ablynx) | Nanobody | IL-17A/F, HSA | Blockade of 2 proinflammatory cytokines, binds to HSA to increase half-life | Phase I | (Healthy volunteers) |
| ALX-0061 (AbbVie, Ablynx; | Nanobody | IL-6R, HSA | Blockade of proinflammatory cytokine, binds to HSA to increase half-life | Phase I/II | Rheumatoid arthritis |

TABLE 3-continued

| Bispecific Formats | | | | | |
|---|---|---|---|---|---|
| Name (other names, sponsoring organizations) | BsAb format | Targets | Proposed mechanisms of action | Development stages | Diseases (or healthy volunteers) |
| ALX-0141 (Ablynx, Eddingpharm) | Nanobody | RANKL, HSA | Blockade of bone resorption, binds to HSA to increase half-life | Phase I | Postmenopausal bone loss |
| RG6013/ACE910 (Chugai, Roche) | ART-Ig | Factor IXa, factor X | Plasma coagulation | Phase II | Hemophilia |

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only and is not intended to limit the invention so further described in such appended claims.

What is claimed:

1. A bioprocess system comprising:

a first bioprocess device;

a second bioprocess device;

a bioprocess tube in fluid communication with the first bioprocess device and the second bioprocess device, the bioprocess tube comprising a thermoplastic elastomer, the bioprocess tube defining a hollow passageway and having an internal diameter, an external diameter, and an external surface, the internal diameter being greater than 260 mm; and a separating collar for facilitating cutting the bioprocess tube for disconnecting the first bioprocess device from the second bioprocess device, the separating collar being slidably mounted on the external surface of the bioprocess tube, the separating collar having a cylindrical shape and having a length that extends from a first end to a second and opposite end, the separating collar defining at least one pair of adjacent separating edges that extend over the length of the collar, the pair of adjacent separating edges allowing the separating collar to be installed and removed from a bioprocess tube, wherein the pair of adjacent separating edges define a slit, the slit having a width greater than 0.5 mm; and wherein the separating collar is made from a metal.

2. The bioprocess system as defined in claim 1, wherein the separating collar is made from a material that is sufficiently rigid and malleable such that when the separating collar is cut with a cutting tool to form cut ends, the cut ends of the separating collar maintain cut ends of the bioprocess tube in a closed configuration.

3. The bioprocess system as defined in claim 1, wherein the metal comprises aluminum.

4. The bioprocess system as defined in claim 1, wherein the width of the slit is less than 3 mm.

5. The bioprocess system as defined in claim 1, wherein the width of the slit is greater than 3 mm and less than 100 mm.

6. The bioprocess system as defined in claim 1, wherein the separating collar comprises a first collar member and a separate second collar member, the first and second collar members cooperating together to form the cylindrical shape.

7. The bioprocess system as defined in claim 6, wherein the separating collar forms two pair of adjacent separating edges where the first collar member intersects the second collar member.

8. The bioprocess system as defined in claim 1, wherein the separating collar has a length of from 600 mm to 10,000 mm.

9. The bioprocess system as defined in claim 1, wherein the first bioprocess device comprises a chromatography device.

10. The bioprocess system as defined in claim 1, wherein the second bioprocess device comprises a filtration device.

11. The bioprocess system as defined in claim 1, wherein the first bioprocess device comprises a chromatography device and the second bioprocess device comprises a filtration device.

12. The bioprocess system as defined in claim 1, wherein the first bioprocess device comprises a filtration device and wherein the second bioprocess device comprises a bioprocess bag.

13. A process for disconnecting two bioprocess devices comprising;

placing a separating collar on an exterior surface of a bioprocess tube, the bioprocess tube being made from a thermoplastic elastomer, the bioprocess tube defining a hollow passageway and having an internal diameter and an external diameter, the internal diameter being greater than 260 mm, the separating collar being slidably mounted on the exterior surface of the bioprocess tube, the separating collar having a cylindrical shape and having a length that extends from a first end to a second end, the separating collar defining at least one pair of adjacent separating edges that extend over the length of the collar that permits placement of the separating collar on the exterior surface of the bioprocess tube, wherein the pair of adjacent separating edges define a slit, the slit having a width greater than 0.5 mm; and cutting through the separating collar and bioprocess tube to produce a first free end and a second free end, wherein during cutting, the separating collar and underlying bioprocess tube are deformed, compressing walls of the bioprocess tube together, the separating collar being made from a metal with sufficient rigidity and malleability to maintain the free ends of the bioprocess tube in a compressed condition after cutting.

14. The process as defined in claim 13, wherein the metal comprises aluminum.

15. The process as defined in claim 13, wherein, after transferring a bioprocess composition through the bioprocess tube from a first bioprocess device to a second bioprocess device, the separating collar and bioprocess tube are cut.

16. The process as defined in claim 15, wherein the first bioprocess device comprises a chromatography device.

17. The process as defined in claim 15, wherein the second bioprocess device comprises a filtration device.

18. The process as defined in claim 17, wherein the filtration device is an ultrafiltration device that filters a bioprocess composition, the filtered composition being fed through the bioprocess tube prior to cutting the tube with the separating collar.

19. The process as defined in claim 15, wherein at least one of the first bioprocess device or the second bioprocess device is connected to the bioprocess tube comprises a bioprocess bag.

20. The process as defined in claim 13, wherein, prior to cutting the bioprocess tube, the process includes blocking flow of fluids through the bioprocess tube upstream of the separating device using a flow stop device and blocking flow of fluids through the bioprocess tube downstream of the separating device using a flow stop device.

21. An apparatus for conveying a bioprocess fluid comprising:

a bioprocess tube made from a thermoplastic elastomer, the bioprocess tube defining a hollow passageway and having an internal diameter, an external diameter and an external surface, the internal diameter of the bioprocess tube being greater than 260 mm; and a separating collar removably mounted on the external surface of the bioprocess tube, the separating collar being mounted such that the separating collar is slidable along the external surface of the bioprocess tube, the separating collar having a cylindrical shape and having a length that extends from a first end to a second end, the separating collar defining at least one pair of adjacent separating edges that extend over the length of the collar, the pair of adjacent separating edges allowing the separating collar to be installed and removed from the bioprocess tube, wherein the pair of adjacent separating edges define a slit, the slit having a width greater than 0.5 mm, the separating collar being made from a rigid and malleable metal that, when a cut is made through the separating collar and the underlying bioprocess tube, the separating collar compresses and maintains cut ends of the bioprocess tube in a closed state after cutting.

* * * * *